US009138265B2

(12) United States Patent
Dauster et al.

(10) Patent No.: US 9,138,265 B2
(45) Date of Patent: Sep. 22, 2015

(54) APPARATUS AND METHOD FOR VISUALIZING INSERTION OF A FIXATION ELEMENT INTO AN IMPLANT

(75) Inventors: Andrew Dauster, Breinigsville, PA (US); Anthony R. Maslowski, Pennsburg, PA (US); Peyman Pakzaban, Pasadena, TX (US); Scott Webb, Clearwater, FL (US)

(73) Assignee: Aesculap Implant Systems, LLC, Center Valley, PA (US)

( * ) Notice: Subject to any disclaimer, the term of this patent is extended or adjusted under 35 U.S.C. 154(b) by 666 days.

(21) Appl. No.: 13/423,673

(22) Filed: Mar. 19, 2012

(65) Prior Publication Data

US 2013/0245633 A1    Sep. 19, 2013

(51) Int. Cl.
*A61B 17/70* (2006.01)
*A61B 1/317* (2006.01)

(52) U.S. Cl.
CPC ............. *A61B 17/7076* (2013.01); *A61B 1/317* (2013.01); *A61B 17/708* (2013.01); *A61B 17/7085* (2013.01); *A61B 17/7035* (2013.01)

(58) Field of Classification Search
CPC .................................. A61B 17/7074–17/7092
USPC ....................................................... 606/86 A
See application file for complete search history.

(56) References Cited

U.S. PATENT DOCUMENTS

| 6,558,390 | B2 * | 5/2003 | Cragg .............................. 606/80 |
|---|---|---|---|
| 7,056,321 | B2 | 6/2006 | Pagliuca |
| 7,179,225 | B2 | 2/2007 | Shluzas |
| 7,226,451 | B2 | 6/2007 | Shluzas |
| 7,270,991 | B2 | 9/2007 | Williamson |
| 7,320,688 | B2 | 1/2008 | Foley |
| 7,326,210 | B2 | 2/2008 | Jahng |
| 7,645,232 | B2 | 1/2010 | Shluzas |
| 7,651,496 | B2 | 1/2010 | Keegan |
| 7,658,739 | B2 | 2/2010 | Shluzas |
| 7,799,833 | B2 | 9/2010 | Boyd |
| 7,819,877 | B2 | 10/2010 | Guzmán |
| 7,892,238 | B2 | 2/2011 | DiPoto |
| 7,935,054 | B2 | 5/2011 | Hamada |
| 7,947,079 | B2 | 5/2011 | Helm |
| 7,976,464 | B2 | 7/2011 | Shluzas |
| 7,985,247 | B2 | 7/2011 | Shluzas |

(Continued)

OTHER PUBLICATIONS

"Aesculap Neurosurgery: MINOP Neuroendoscopy Systems", Aesculap (2009), 24 pgs.

*Primary Examiner* — Jerry Cumberledge
*Assistant Examiner* — Nicholas Plionis
(74) *Attorney, Agent, or Firm* — RatnerPrestia

(57) ABSTRACT

Apparatuses and methods for inserting elongated fixation elements into screw implants include one or components for visualizing the insertion process from a unique vantage point. One apparatus features a steering apparatus for adjusting the position of a receiver element on a screw implant, so that an elongated fixation element, such as a rod, can be inserted through a transverse passage in the receiver element. The steering apparatus may include an extension tube and a steering control member coupled to the extension tube. The extension tube may be configured for coupling to the receiver element, and the steering control member may be configured for coupling to the extension tube. The steering control member may include an opening for receiving an endoscope. The endoscope may be used to visually monitor the elongated fixation element as it is inserted into the transverse passage of the receiver element.

13 Claims, 10 Drawing Sheets

(56) References Cited

U.S. PATENT DOCUMENTS

| | | |
|---|---|---|
| 7,988,623 B2 | 8/2011 | Pagliuca |
| 7,993,370 B2 | 8/2011 | Jahng |
| 7,993,378 B2 | 8/2011 | Foley |
| 8,002,743 B2 | 8/2011 | Miller |
| 8,012,187 B2 | 9/2011 | Sherman |
| 8,012,207 B2 | 9/2011 | Kim |
| 8,016,828 B2 | 9/2011 | Shluzas |
| 8,016,835 B2 | 9/2011 | Birkmeyer |
| 8,021,426 B2 | 9/2011 | Segal |
| 8,034,055 B2 | 10/2011 | Cragg |
| 8,034,088 B2 | 10/2011 | Pagano |
| 8,043,212 B1 | 10/2011 | Bae |
| 8,043,376 B2 | 10/2011 | Falahee |
| 8,057,472 B2 | 11/2011 | Walker |
| 8,062,300 B2 | 11/2011 | Schmitz |
| 8,066,705 B2 | 11/2011 | Michelson |
| 2004/0215190 A1* | 10/2004 | Nguyen et al. ................ 606/61 |
| 2007/0078460 A1* | 4/2007 | Frigg et al. .................... 606/61 |
| 2009/0143829 A1 | 6/2009 | Shluzas |
| 2010/0331883 A1* | 12/2010 | Schmitz et al. .............. 606/249 |
| 2011/0178560 A1* | 7/2011 | Butler et al. ................ 606/86 A |
| 2011/0245620 A1 | 10/2011 | Hamada |
| 2011/0245836 A1 | 10/2011 | Hamada |

\* cited by examiner

APPARATUS AND METHOD FOR VISUALIZING INSERTION OF A FIXATION ELEMENT INTO AN IMPLANT

FIELD

The field of the invention relates generally to bone fixation implants, and more specifically to apparatuses and methods for visually confirming the insertion of a fixation element, such as a rod, into an implant.

BACKGROUND

A number of spinal stabilization systems are currently available for use in the lumbar spine to provide stabilization of the spine during spinal fusion. Many stabilization systems include some type of screw implant, which usually consists of a bone screw and a receiver body attached to the screw. The screw is designed to be inserted into a vertebral body or other bone structure to be stabilized. The receiver body is designed to receive an elongated fixation element, such as a rod. Typically, the receiver body has a transverse passage formed by slots or openings for receiving the rod. The rod is inserted into the transverse passages of two or more screw implants, forming a rigid bridge between the implants. The rod may be introduced using a "captured" technique or a freehand technique. In the captured technique, a guidance device with a defined range of motion controls the path of the rod as it is introduced into the implants. In the freehand technique, the rod is inserted and maneuvered into the implant by hand. Once the rod is inserted into the implants, set screws or other locking elements are used to lock down the rod in the receiver bodies. The rigid bridge construct is used to stabilize adjacent vertebrae and promote bone fusion.

In some procedures, the screw implants and fixation rod are implanted in an open surgical method, where the skin of the patent is incised from the cranial aspect of the area to the caudal aspect. Open incisions of this type occasionally result in significant incision length. Of greatest concern, when examining the open technique, is the trauma to the muscles, nerves, and other soft tissue of the back. This trauma results in biomechanical instability, greater possible necrosis, and an increased time for recovery. Trauma can be reduced by using minimally invasive surgery (MIS), which involves the use of smaller incisions, and muscle splitting rather than cutting. Percutaneous surgery is one form of MIS that utilizes very small stab incisions for the introduction of the screw into the patient. In percutaneous surgery, the screw implants and/or rods are inserted into the patient through small tubes sometimes referred to as downtubes or extension tubes. Extension tubes can be connected to the screw implants to serve as temporary extensions of the screw body. The extensions provide a conduit through the surface of the patient's skin, and provide access to the surgical site through a very small opening. Extension tubes are disconnected from the screw implants and removed from the patient once the surgery is complete.

MIS screw systems offer the advantage of reducing trauma to the patient by minimizing the size of incisions. Nevertheless, the small incisions create a major challenge. MIS screw implants are difficult to see after implantation because the implants are covered by skin and tissue above implants. This makes it difficult or impossible for the surgeon to see the transverse passage of the implant and the rod during rod insertion. The relative position of the rod can be monitored using fluoroscopy. But even where fluoroscopy is used, depth perception is very limited when watching the image. As such, it is difficult to determine whether the rod is passing through the transverse passage of the receiver body as intended. In some instances, the rod may appear to be passing through the receiver body, when in fact it is passing in front of or behind the receiver body. It is not uncommon to find that the rod has passed along the outside edge of the receiver body, necessitating the total removal and replacement of the rod.

Even when imaging techniques are available, there is still a need for better ways to visualize the introduction of the rod into the receiver body, so that the proper placement of the rod can be confirmed.

SUMMARY

The drawbacks of conventional rod insertion techniques are resolved in many respects with apparatuses and methods in accordance with the invention. In one embodiment, an apparatus for visualizing insertion of a fixation element into a screw implant features an extension tube and a steering control member. The extension tube has a proximal end and a distal end opposite the proximal end. The distal end of the extension tube may be configured for coupling to a receiver element that is connected to a bone screw. The steering control member may include a proximal end and a distal end opposite the proximal end. The distal end of the steering control member may be permanently attached to or detachably coupled to the proximal end of the extension tube. The proximal end of the steering control member may include an opening for receiving an endoscope inside the steering control member.

The steering control member may feature a main body and a handle extending laterally from the main body. The main body may surround a hollow interior inside the steering control member. The steering control member may include a tubular extension on the main body that forms a port in fluid communication with the hollow interior of the steering control member. The distal end of the steering control member may include a plug extending from the main body, the plug configured for insertion into the proximal end of the extension tube.

The steering control member and extension tube may include elements for coupling the steering control member and extension tube together. For example, the plug may include a radial projection, and the proximal end of the extension tube may include a slot configured to receive the radial projection to interconnect the steering control member and extension tube. The projection and slot may fix the orientation of the extension tube relative to the steering control member so that the steering control member and extension tube are rotatable in unison about a longitudinal axis defined by the extension tube. The radial projection may advantageously include an elongated tab extending axially along the plug. The slot may advantageously include an elongated slot section conforming to the shape of the elongated tab.

The apparatus may further include an endoscope to assist in visualizing a fixation element as it is introduced into the transverse passage of a receiver element. The endoscope may be inserted through the steering control member and into the extension tube. The apparatus may also feature an irrigation/suction device inserted through the steering control member and into the extension tube.

In another embodiment, a method for inserting an elongated fixation element into a screw implant includes the step of attaching a distal end of a steering apparatus to a proximal end of a receiver body associated with a screw implant. The steering apparatus may include a hollow interior providing a line of sight into a transverse passage in the receiver body. The distal end of the steering apparatus may also include a transverse passage. An endoscope may be inserted into the hollow interior and line of sight of the steering apparatus. The endoscope may be positioned so that the transverse passages of the steering apparatus and receiver body are visible in the field of view of the endoscope. The elongated fixation element may then be brought into the field of view and navigated through the transverse passages of the steering apparatus and receiver body while the position of the elongated fixation element is visually monitored through the endoscope.

In another embodiment, a method for inserting an elongated fixation element into a screw implant includes the step of attaching a distal end of an extension tube to a proximal end of a receiver body associated with a screw implant. The extension tube may have a hollow interior providing a line of sight into a transverse passage in the receiver body. A steering control member may be attached to a proximal end of the extension tube, the steering control member having a main body with a hollow interior in communication with the hollow interior in the extension tube. An endoscope may be inserted through the hollow interior of the main body of the steering control member and into the hollow interior and line of sight in the extension tube. The endoscope may be positioned so that transverse passages of the extension tube and receiver body are visible in the field of view of the endoscope. The elongated fixation element may then be guided into the field of view and navigated through the transverse passages of the extension tube and receiver body. The position of the elongated fixation element may be visually monitored through the endoscope.

The method may include the step of aligning a transverse passage of the receiver body with a transverse passage of the extension tube so that the transverse passage of the receiver body passes through the transverse passage of the extension tube. Moreover, the method may include the step of aligning the transverse passage of the receiver body with the transverse passage of the extension tube so that the transverse passage of the receiver body is parallel to the transverse passage of the extension tube.

The method may also include the step of attaching the distal end of the extension tube to the proximal end of the receiver body, which may include the step of coupling the distal end of the extension tube to the proximal end of the receiver body so that the extension tube and receiver body are moveable in unison relative to the screw.

The method may further include the step of attaching the steering control member to the proximal end of the extension tube, which may include the step of coupling a distal end of the steering control member to the proximal end of the receiver body so that the steering control member, extension tube and receiver body are moveable in unison relative to the screw.

The method may include the step of rotating the steering control member to orient the transverse passages of the extension tube and receiver member into positions to receive the elongated fixation element, prior to navigating the elongated fixation element through the transverse passages.

The method may also include the step of rotating the steering control member to orient the transverse passages of the extension tube and receiver member into alignment with a proposed path of trajectory for the elongated fixation member. In addition, or as an alternative, the method may include the step of tilting the steering control member to orient the transverse passages of the extension tube and receiver member into positions to receive the elongated fixation element. Moreover, the method may include the step of tilting the steering control member to orient the transverse passages of the extension tube and receiver member into alignment with a proposed path of trajectory for the elongated fixation member.

The method may also include the step of moving the steering control member, extension tube and receiver body in unison relative to the screw by manually gripping a handle extending from the steering control member and applying force to the handle in one or more directions transverse to a longitudinal axis passing through the extension tube.

Furthermore, the method may include the step of attaching the steering control member to the proximal end of the extension tube, which includes the step of inserting a radial projection on the steering control member into a slot in the proximal end of the extension tube to couple the steering control member to the extension tube.

BRIEF DESCRIPTION OF THE DRAWINGS

The foregoing summary and the following detailed description will be better understood in conjunction with the drawing figures, of which.

DETAILED DESCRIPTION OF THE PREFERRED EMBODIMENTS

Figure 1:
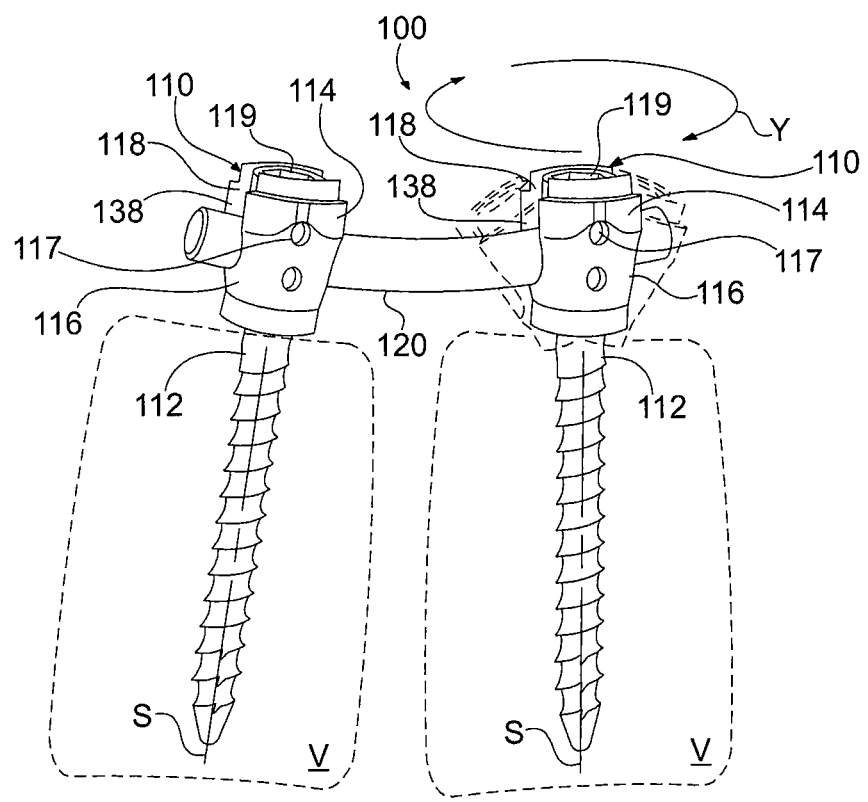
FIG. 1 is a perspective view of a bone fixation assembly featuring screw implants and a fixation rod that may be inserted into the screw implants using apparatuses and methods in accordance with the invention.

Although this description makes reference to specific embodiments and illustrations, the invention is not intended to be limited to the details shown. Rather, the invention encompasses various modifications and combinations of the specific embodiments and illustrations that may be made within the scope and range of equivalents of the claims.

The drawbacks of conventional rod insertion techniques are resolved in many respects with apparatuses and methods in accordance with the invention that provide a unique vantage point for visually monitoring a rod insertion procedure. This unique vantage point allows the rod and the transverse passage of the implant to be viewed during rod insertion. More specifically, the vantage point allows the surgeon to view the relative position and orientation of the transverse passage with respect to the location and orientation of the rod, and with respect to the location of other implants. From this vantage point, the surgeon can visually confirm that a rod is successfully inserted through an implant, or alternatively, to troubleshoot problems with the screw implant. For example, the surgeon can see and correct problems affecting the connection of the extension tube with the implant, or problems that prevent proper insertion of the set screw or other locking element. Furthermore, the vantage point allows the surgeon to detect when the orientation and/or position of the receiver element is not aligned with the rod, preventing rod insertion. As such, apparatuses and methods in accordance with the invention provide an enhanced view of the rod and its passage through the screw implant. This enhanced view simplifies the rod insertion procedure and reduces time in the operating room.

In most cases, the vantage point is directly above the pedicle screw implant, looking down through the extension tube. The vantage point allows the surgeon to see the location of the slots in the receiver body and confirm that they are properly arranged so that the transverse passage is oriented to receive the rod prior to insertion. In addition, the vantage point allows the surgeon to see the transverse passage and rod together from a "birds eye" view so that the surgeon can confirm that the rod is passing through the transverse passage as intended. The transverse passage and rod may be visually monitored with the aid of an endoscope inserted down into the extension tube. Apparatuses and methods in accordance with the invention can be used with either the captured technique or the freehand technique for inserting a rod.

Apparatuses and methods in accordance with the invention can be used to navigate rods and other elongated fixation elements through surgical implants that are implanted in the body of a human or animal. This description focuses primarily on examples of implants used in the human spine, and more specifically, on pedicle screw implants. Apparatuses and methods in accordance with the invention may be used with pedicle screw implants that are either monoaxial or polyaxial. For purposes of this description, the term "monoaxial" means a pedicle screw implant in which the receiver element has a fixed orientation relative to the screw. That is, the receiver element has a longitudinal axis that is fixed with respect to the screw's longitudinal axis. The receiver element may rotate on its own fixed axis, but it cannot tilt to any other axis with respect to the axis of the screw. The term "polyaxial", in contrast, means a pedicle screw implant in which the receiver element is free to pivot or tilt to any axis with respect to the longitudinal axis of the screw.

FIG. 1 shows one example of a known pedicle screw and rod assembly 100 with which the apparatuses and methods described herein may be used. Assembly 100 includes two pedicle screw implants 110 and a fixation rod 120 bridging the pedicle screw implants. Each pedicle screw implant 110 includes a screw 112 implanted into the pedicle portion of a vertebra V. Each screw 112 has a rounded head (not shown), such as a spherical head, that is seated inside a rod receiving element or "receiver element" 114. Each receiver element 114 has a generally cylindrical receiver body 116 that is hollow in the center. Each receiver body 116 has a pair of bores 117 on its exterior for engagement with instrumentation. Each receiver body 116 also has a pair of diametrically opposed slots 118 that are "U"-shaped. Slots 118 form a transverse passage 138 through receiver element 114. Each transverse passage 138 is configured to receive rod 120 to bridge the two implants 110 together.

Rod 120 can be locked down in each receiver element 114 with a set screw 119. Each set screw 119 can be threaded into a receiver element 114 and rotated as needed to move the set screw between a locked position, in which the set screw contacts and holds down rod 120, and an unlocked position in which the set screw does not contact the rod. The rounded geometry of the screw head allows each receiver element 114 to move polyaxially with respect to its respective screw when the rod is not locked down in the receiver element. Area Y illustrates one possible range of polyaxial motion relative to longitudinal axis S of screw 110.

The perspective view of FIG. 1 shows that rod 120 is inserted through each receiver element 114. A similar perspective view provided under fluoroscopy would not depict the rod and receiver elements with the same degree of clarity. In many cases, a side view provided by fluoroscopy can mislead one into thinking that the rod is inserted through each receiver body, when in fact the rod passes in front of or behind the receiver body. Apparatuses and methods described herein can be used as a primary method for monitoring rod insertion, or as a supplemental aid to confirm that the rod is properly inserted through receiver elements.

Figure 2:
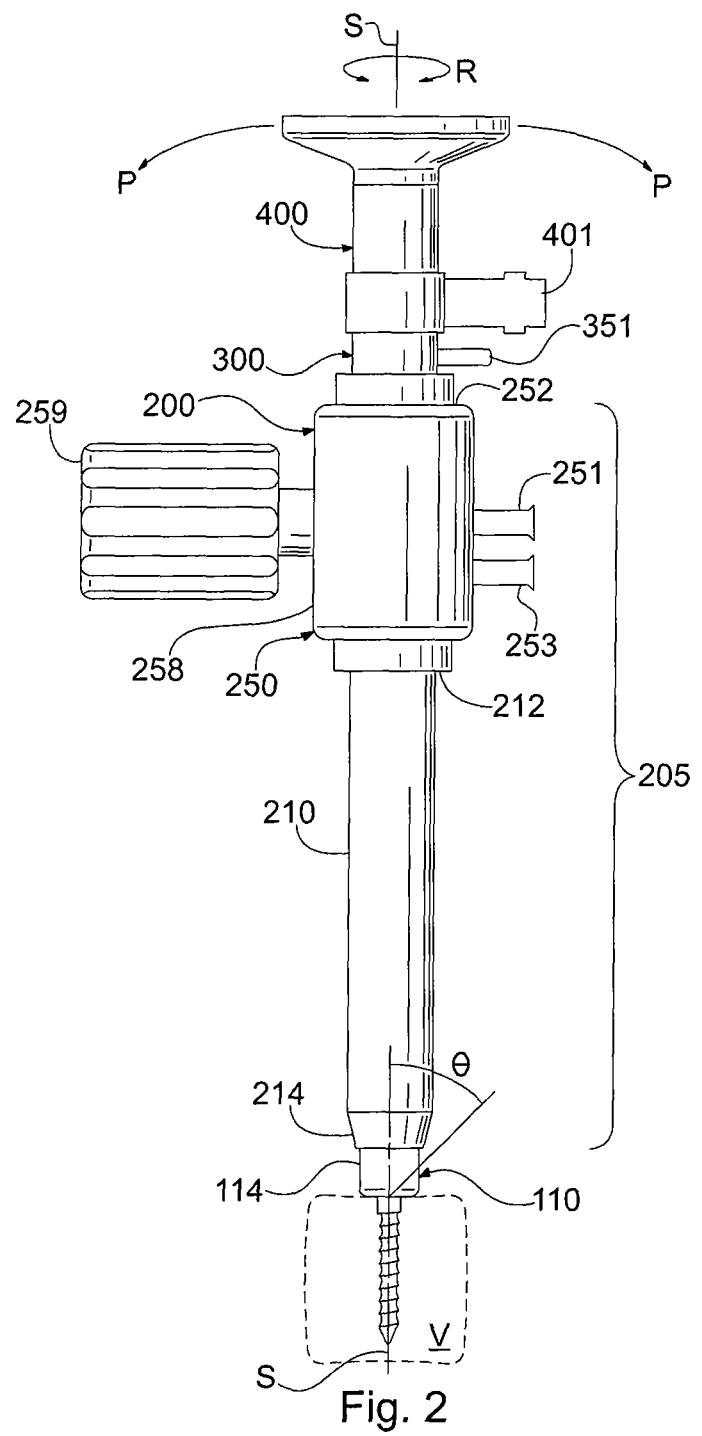
FIG. 2 is a side elevation view of an apparatus in accordance with one exemplary embodiment, the apparatus schematically shown engaged with a screw implant.
Figure 3:
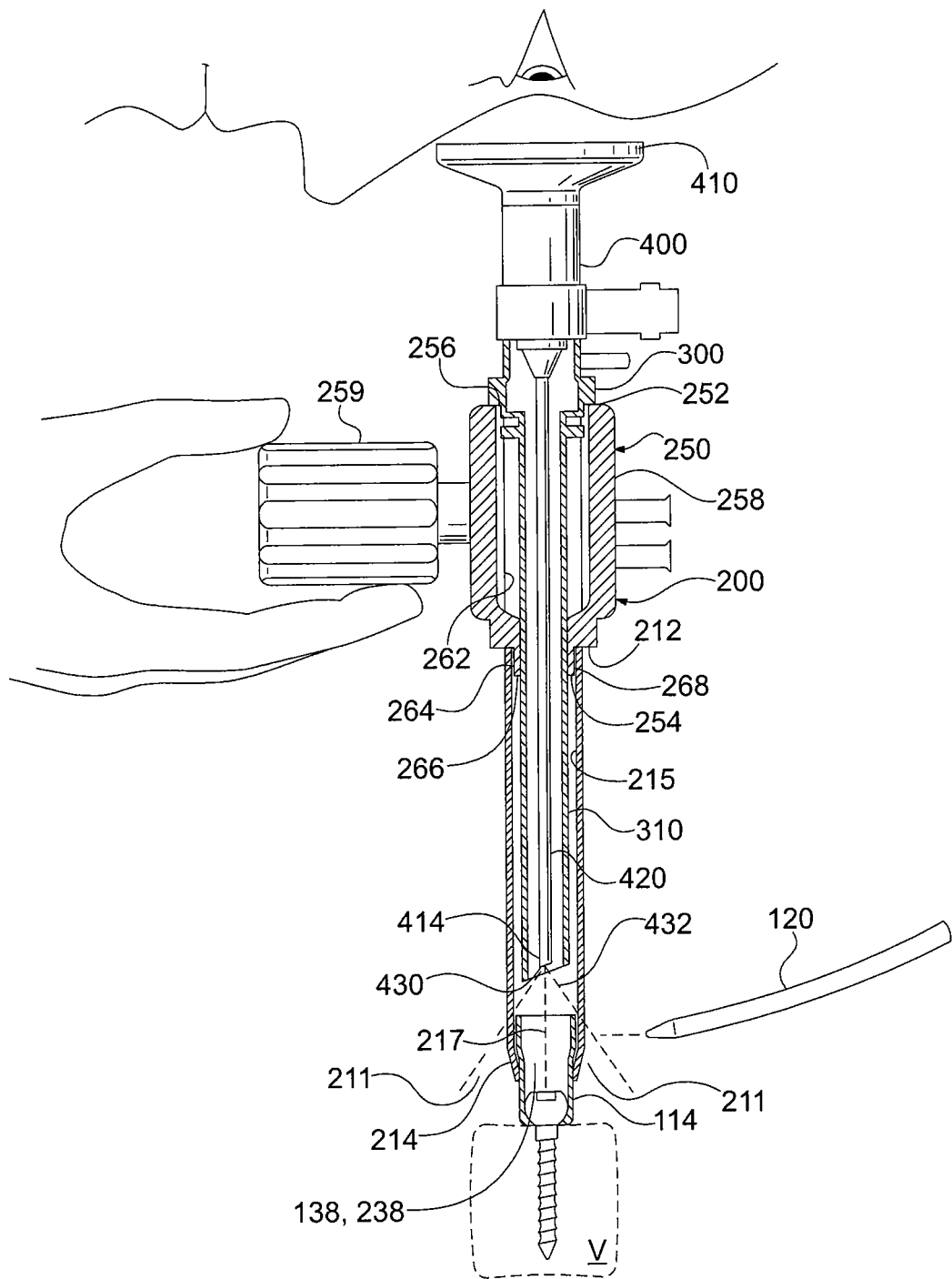
FIG. 3 is a side elevation view in partial cross-section, showing the apparatus and screw implant of FIG. 2.

FIGS. 2 and 3 illustrate one apparatus 200 for visualizing insertion of a rod or other fixation element into a screw implant. Apparatus 200 allows a surgeon to look directly down into a receiver element to see the transverse passage through the receiver element, and areas immediately outside the receiver element. This bird's eye view allows the surgeon to see the position and orientation of the transverse passage relative to a rod before the rod is inserted into the passage. The surgeon can adjust the position and/or orientation of the rod receiver element so that the rod can be properly inserted through the transverse passage. In the case of a monoaxial screw implant, the surgeon can rotate the receiver element to align the slots and transverse passage with the rod. In the case of a polyaxial screw implant, the surgeon can both rotate and pivot (tilt) the receiver element on the screw head to align the slots and transverse passage with the rod.

Apparatus 200 includes a steering apparatus 205. As will be described in more detail below, steering apparatus 205 is operable to engage a receiver element 114 and adjust its orientation and/or position so that a rod can be passed through the receiver element. Steering apparatuses in accordance with the invention may comprise a single component, or multiple components assembled together. Steering apparatus 205, for example, includes an extension tube 210 and a steering control member 250. Extension tube 210 has a proximal end 212 and a distal end 214 opposite the proximal end. Distal end 214 of extension tube 210 is configured for coupling to a receiver element that may be monoaxially or polyaxially connected to a bone screw. As noted earlier, screw implant 110 is a polyaxial screw implant.

Extension tube 210 is configured to detachably connect to the rod receiver element 114 of screw implant 110. Distal end of 214 of extension tube 210 has one or more engagement tabs (not shown) that snap into the bores 117 on the exterior of receiver body 116. When the tabs are engaged in bores 117, extension tube 210 is detachably coupled to, and moveable in unison with, the rod receiver element 114.

Figure 6:
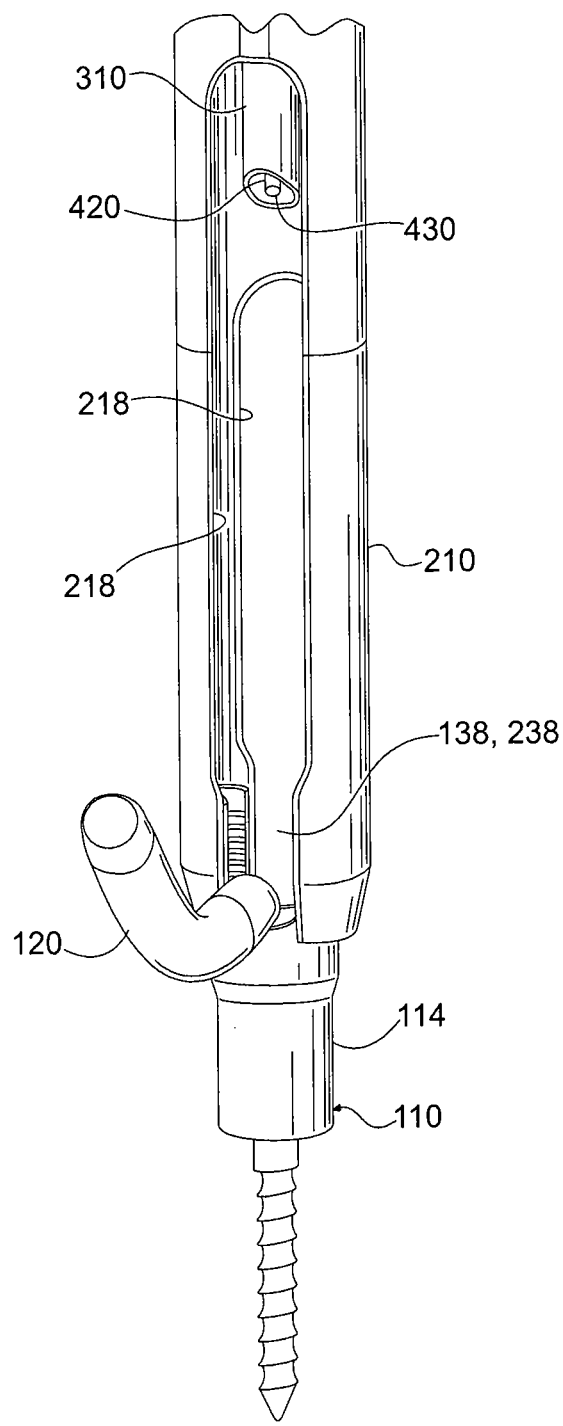
FIG. 6 is an enlarged perspective view of components of the apparatus of FIG. 2, with portions of some components truncated for clarity, showing a screw implant and a rod to be inserted in the screw implant.

Referring to FIG. 6, extension tube 210 forms a pair of diametrically opposed slots 218 that are configured to overlap the opposed slots 118 of screw implant 110 when distal end 214 of the extension tube is connected to the screw implant. Slots 218 form a transverse passage 238 through the extension tube, similar to transverse passage 138 in receiver element 110. Slots 218 on extension tube 210 are positioned to align with and overlap with slots 118 of screw implant 110. When the tabs inside extension tube 210 engage bores 117 on the exterior of receiver element 114, slots 218 are axially aligned with slots 118. Once slots 218 are aligned with slots 118, transverse passage 238 coincides with and extends parallel to transverse passage 138, allowing the insertion of a rod 120 through extension tube 210 and receiver element 114.

Figure 4:
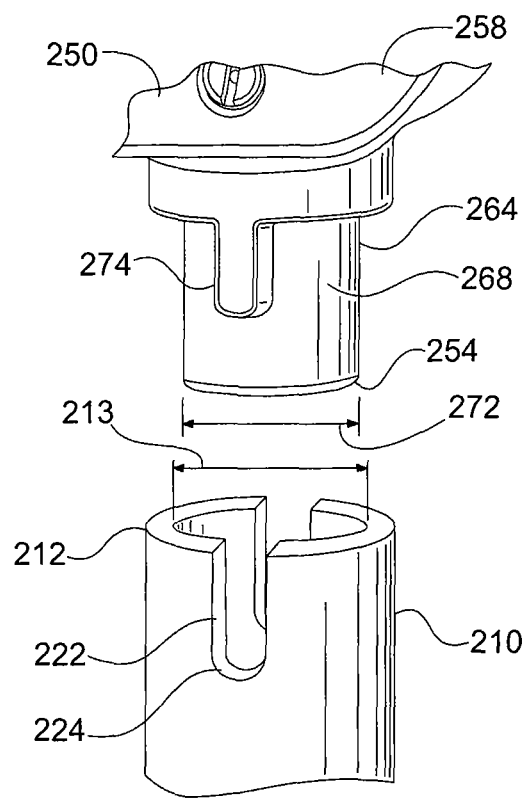
FIG. 4 is an enlarged perspective view of two components of the apparatus of FIG. 2, with portions truncated for clarity, the components shown in a disassembled condition.

Referring to FIGS. 2-4, steering control member 250 includes a proximal end 252 and a distal end 254 opposite the proximal end. Distal end 254 of steering control member 250 is configured for coupling to proximal end 212 of extension tube 210. Proximal end 252 of steering control member 250 forms an opening 256 for receiving a device, such as an endoscope, inside the steering control member. Steering control member 250 includes a main body 258 and a handle 259 extending laterally from the main body. Main body 258 forms a hollow interior 262 inside steering control member 250. Steering control member 250 also includes a tubular extension 264 forming a port 266 at distal end 254. Port 266 extends in fluid communication with hollow interior 262 of steering control member 250. Tubular extension 264 forms a plug 268 extending from main body 258. Plug 268 has a generally cylindrical geometry with an outer diameter 272. Outer diameter 272 is equal to or slightly less than an inner diameter 213 of extension tube 210 at its proximal end 212. This allows plug 268 to be inserted into proximal end 212 of extension tube 210 in a snug fit. Steering control member 250 also includes a first port 251 for suction and a second port 253 for irrigation.

Figure 5:
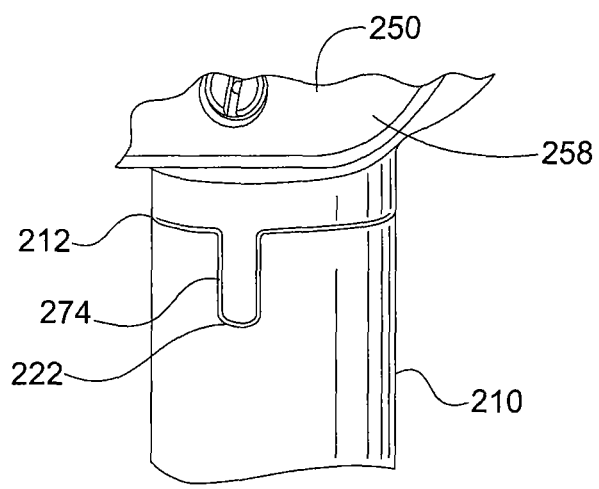
FIG. 5 is an enlarged perspective view of the two components of FIG. 4, with portions truncated for clarity, showing the components in an assembled condition.

Apparatuses in accordance with the invention preferably include engagement features that lock the orientation of the steering control member relative to the orientation of the extension tube when the two are connected. When the steering control member and extension tube are locked together in this manner, rotation and/or pivoting of the steering control member rotates and/or pivots the extension tube and rod receiver element in unison with the steering control member. Referring to FIGS. 4 and 5, plug 268 includes a pair of radial projections in the form of elongated tabs 274 (only one of which is visible). Proximal end 212 of extension tube 210 comprises a pair of slots 222, the slots having slot sections 224 that conform to the shapes of the tabs 274. Slots 222 are configured to receive tabs 274 to interconnect steering control member 250 and extension tube 210. Tabs 274 are slidable axially, or along the long dimensions of slots 222, but cannot move transversely to the long dimensions of the slots.

The confinement of tabs 274 in slots 222 fixes the orientation of extension tube 210 relative to steering control member 250. In the case of a monoaxial screw implant, steering control member 250 and extension tube 210 are rotatable in unison about a longitudinal axis S defined by the screw shaft. The direction of rotation is shown by the arrow R in FIG. 2. In the case of a polyaxial screw implant, steering control member 250 and extension tube 210 are rotatable and pivotable (i.e. able to tilt) with respect to longitudinal axis S of the screw shaft. In the latter case, steering control member 250 is maneuverable to pivot (or tilt) the extension tube 210 and receiver element 114 in the medial direction, lateral direction, cranial direction, caudal direction, or a combination of directions. Examples of pivot directions are shown by the arrows P in FIG. 2. Precise rotation and/or pivoting of the extension tube allows the endoscope to be focused on the transverse passage as the rod is guided through the passage. This process, described in more detail below, allows for easier navigation of a rod through receiver element 114.

Apparatus 200 includes an irrigation/suction trocar 300 and an endoscope 400. Irrigation/suction trocar 300 includes an elongated hollow shaft 310 that extends through steering control member 250 and into extension tube 210. Endoscope 400 includes an eyepiece 410 and en elongated shaft 420. Shaft 420 has an outer diameter that is smaller than the inner diameter of shaft 310, allowing the shaft of the endoscope 400 to be inserted through the shaft of irrigation/suction trocar 300. Irrigation/suction trocar 300 includes a port 351, and endoscope 400 includes a port 401. Ports 351 and 401 provide alternatives to first and second ports 251 and 253 on steering control member for irrigation and suction.

Referring now to FIGS. 3 and 6, extension tube 210 has a hollow interior 215. Hollow interior 215 provides a line of sight 217 into the transverse passage 138 of the receiver element 114. Shaft 420 of endoscope 400 has a distal end 414 with a lens 430. Lens 430 provides a field of view 432 that captures the area inside rod receiver element 120 and the vicinity around the rod receiver element. Field of view 432 encompasses the transverse passages 138 and 238 of receiver element 114 and extension tube 210, respectively, and the spaces 211 immediately outside the slots of the extension tube.

Methods of visualizing the insertion of a rod or other elongated fixation element into a screw implant will now be described. In describing the methods, reference may be made to one or more components of apparatus 200. It will be understood, however, that the methodology described in this section can be practiced using apparatuses with different features and characteristics. Apparatus 200 is just one possible apparatus that may be used to visualize the insertion of a rod.

Figure 12:
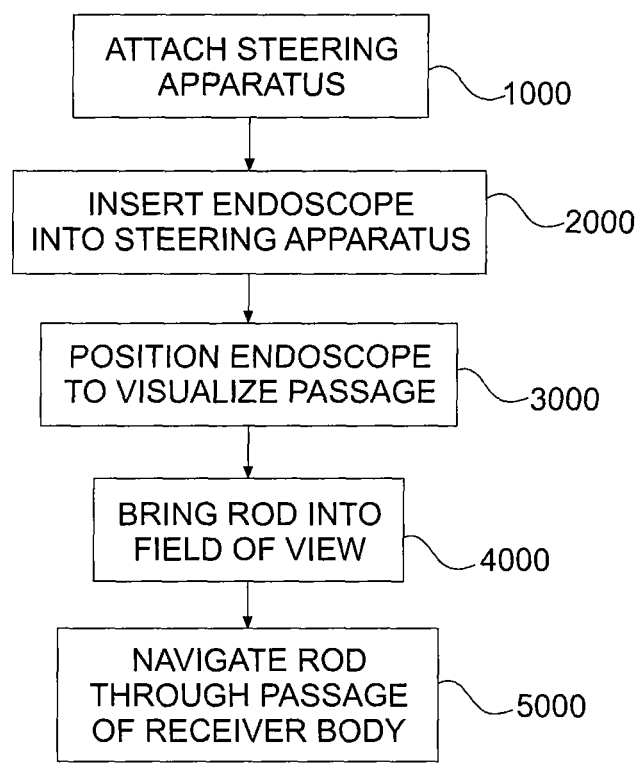
FIG. 12 is a block diagram of steps for inserting an elongated fixation element into a screw implant in accordance with one possible method of the invention.

Referring to FIG. 12, a general method for inserting a rod into a screw implant includes the step of attaching a steering apparatus to a receiver body in step 1000. The receiver body each has a transverse passage for receiving the rod. The steering apparatus has a hollow interior that provides a line of sight into the receiver body. An endoscope is inserted into the hollow interior and line of sight of the steering apparatus in step 2000. In step 3000, the endoscope is positioned so that the transverse passage of the receiver body is visible in the field of view of the endoscope. The rod is then brought into the field of view of the endoscope in step 4000. Depending on where the rod is located relative to the receiver body, this step may include moving the rod and/or moving the receiver body so that the rod is visible through the slots in the wall of the receiver body. In step 5000, the rod is navigated through the transverse passage of the receiver body while the position of the rod is visually monitored through the endoscope.

Figure 13:
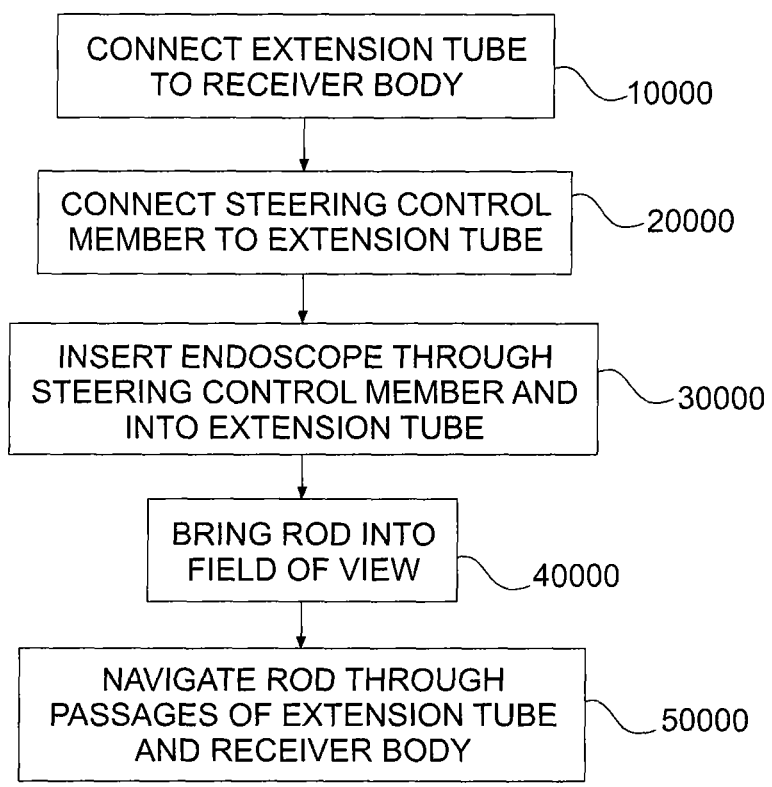
FIG. 13 is a block diagram of steps for inserting an elongated fixation element into a screw implant in accordance with another possible method of the invention.

Referring to FIG. 13, another method of visualizing the insertion of a rod or other elongated fixation element into a screw implant is described. In this method, the steering apparatus is the multi-component apparatus in apparatus 200, which includes the extension tube 210 and steering control member 250. Extension tube 210 is connected to receiver body 114 of screw implant 110 in step 10000. Steering control member 250 is connected to extension tube 210 in step 20000. To connect steering control member 250 to extension tube 210, tabs 274 are aligned with slots 222 in the proximal end of the extension tube, and inserted into the slots. Endoscope 400 is then inserted through the hollow interior of steering control member 250 and into the hollow interior and line of sight in extension tube 210 in step 30000. Endoscope 400 is positioned in step 40000 so that transverse passages 138, 238 of extension tube 210 and receiver body 116 are visible in the field of view 432 of the endoscope.

In step 50000, the rod is brought into the field of view. Depending on where the rod is located relative to the receiver body, this step may include moving the rod and/or moving the extension tube and receiver body so that the rod is visible through the slots in the walls of the extension tube and receiver body. In the preferred method, the field of view captures the transverse passages and the areas immediately outside the slots 218, so that the rod can be seen through the endoscope before it enters the receiver element. The rod is then navigated through the transverse passages of the extension tube and receiver body in step 60000. During this step, the position of the rod relative to the transverse passages may be visually monitored through the endoscope.

The foregoing steps can be performed in different sequences, and need not be performed in the order shown in FIG. 12. For example, the step of connecting steering control member 250 to extension tube 210 (step 20000) can be completed before or after the step of connecting the extension tube to the implant (step 10000).

As the distal end 214 of extension tube 210 is connected to receiver body 116 in step 1000, transverse passage 138 of the receiver body is aligned with transverse passage 238 of the extension tube so that the transverse passage of the receiver body passes through or coincides with the transverse passage of the extension tube. Transverse passages 138, 238 may be perfectly aligned so that the transverse passages are parallel to one another. This is not a requirement, however, as the rod can still pass through the transverse passages 138, 238 even if the passages are not perfectly aligned and parallel to one another.

The attachment of the extension tube 210 to the receiver body 114 will make the extension tube and receiver body moveable in unison relative to the screw. When steering control member 250 is added on to extension tube 210, the steering control member, extension tube and receiver element 114 are all interconnected and moveable in unison relative to screw 112. Steering control member 250 can be rotated about the longitudinal axis S of screw 112 to rotate transverse passages 138, 238 into the proper orientation to receive rod 120. In the case of polyaxial screw implants, steering control member 250 can also be tilted (pivoted) through an angle of displacement θ relative to the longitudinal axis S of screw 112. This tilting can also help in positioning transverse passages 138, 238 in the proper locations to receive rod 120. The orientations of transverse passages 138, 238 and the position of rod 120 outside extension tube 210 can be monitored through endoscope 400.

Figure 7:
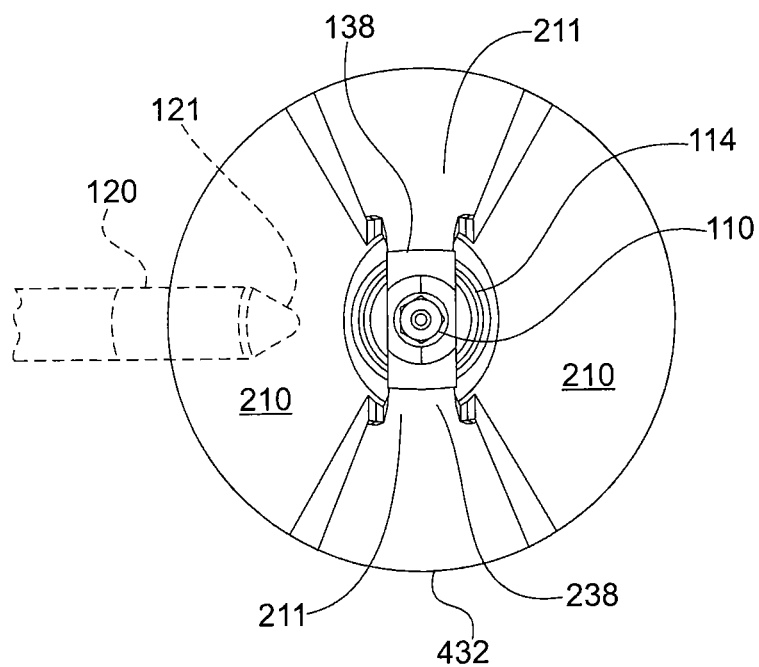
FIG. 7 is a perspective view looking down through components of the apparatus of FIG. 2 and into a screw implant, with portions of some components truncated for clarity, showing a rod to be inserted into the screw implant, with the apparatus, screw implant and rod shown in a first arrangement.
Figure 8:
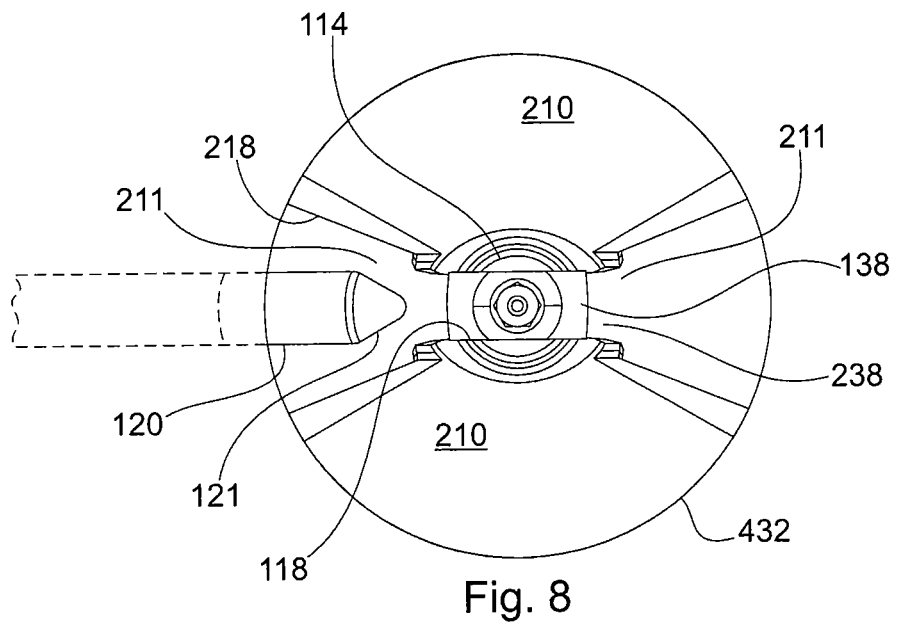
FIG. 8 is a perspective view looking down through components of the apparatus of FIG. 2 and into a screw implant, with portions of some components truncated for clarity, showing a rod to be inserted into the screw implant, with the apparatus, screw implant and rod shown in a second arrangement.
Figure 9:
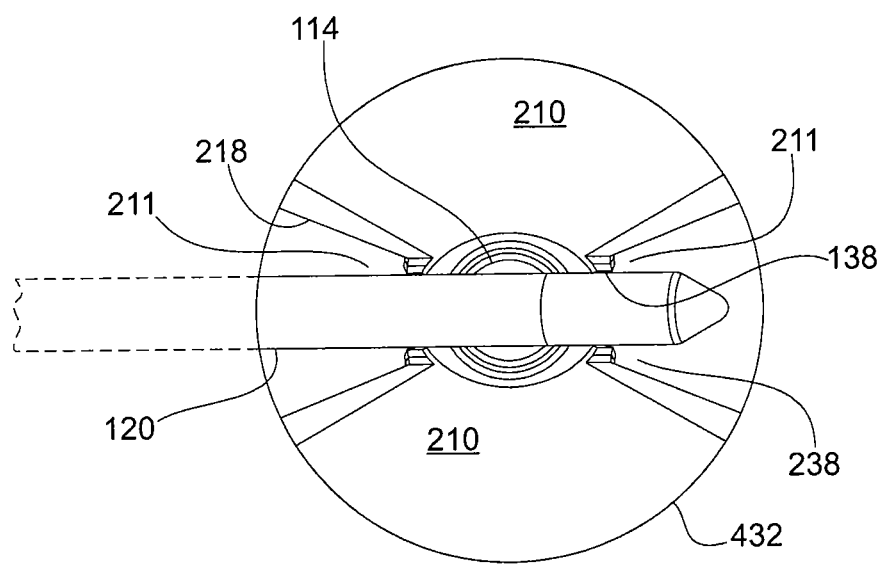
FIG. 9 is a perspective view looking down through components of the apparatus of FIG. 2 and into a screw implant, with portions of some components truncated for clarity, showing a rod to be inserted into the screw implant, with the apparatus, screw implant and rod shown in a third arrangement.

FIGS. 7-9 show one scenario in which steering control member 250 is used to move the transverse passages 138, 238 into the proper orientation to receive rod 120. FIG. 7 represents a field of view 432 provided by endoscope 400 (not visible in FIGS. 7-9) that encompasses the transverse passages 138, 238 and areas 211 just outside the slots 118, 218. Rod 120 is advanced into the proximity of extension tube 210 and stopped just outside the extension tube. Transverse passages 138, 238 are not aligned with rod 120. Therefore, a leading end 121 of rod 120 is not visible in field of view 432. Steering control member 250 (not visible) is slowly rotated until leading end 121 of rod 120 becomes visible through the slots in field of view 432. At this point, transverse channels 138, 238 are oriented so that the rod can be slowly inserted into implant 110. FIG. 8 shows the transverse passages 138, 238 rotated into alignment with rod 120, with the leading end 121 of the rod visible through slots 218 of extension tube 210.

Once transverse passages 138, 238 are aligned with rod 120, the rod is advanced into the transverse passages and through receiver element 114, as shown in FIG. 9. Rod 120 and transverse passages 138, 238 can be visually monitored through endoscope 400, and adjusted as needed, as the rod is advanced into implant 110.

Apparatuses like apparatus 200 can be used to adjust rod receiver elements for multiple screw implants in a series. Apparatus 200 can be used to align the transverse passage of a receiver element with a rod, as described above. In addition, apparatus 200 can be used to steer the transverse passage of a receiver element toward an adjacent implant in a series. In the case of a monoaxial screw implant, the term "steer" means rotating the receiver element so that the direction of the transverse passage is oriented toward a desired target or course, such as a direction leading to an adjacent implant. In the case of a polyaxial screw implant, the term "steer" means rotating the receiver element, pivoting the receiver element, or a combination of rotating and pivoting the receiver element, so that the direction of the transverse passage is oriented toward a desired target or course, such as a direction leading to an adjacent implant. Steering may be done before or after the rod is inserted through the receiver element.

Figure 10:
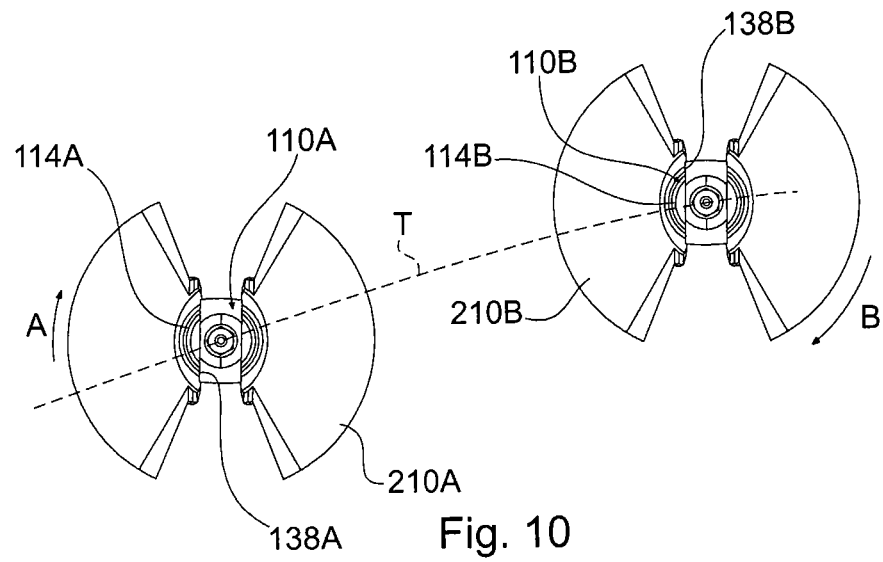
FIG. 10 is a plan view showing two screw implants prior to being aligned with a proposed rod trajectory in accordance with the invention.
Figure 11:
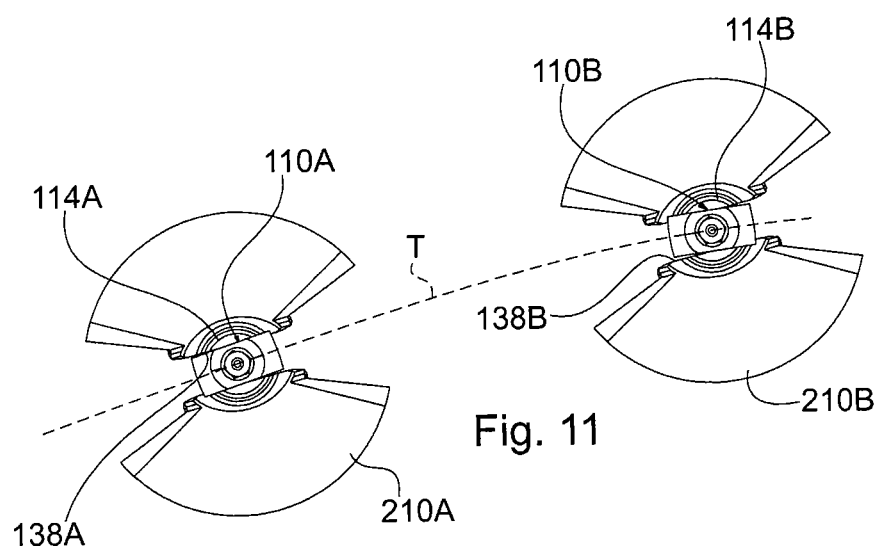
FIG. 11 is a plan view of the screw implants of FIG. 10 after being aligned with a proposed rod trajectory in accordance with the invention.

FIGS. 10 and 11 illustrate an example of how apparatuses and methods in accordance with the invention can be used to steer one or more screw implants. In FIG. 10, a first screw implant 110A is shown with a receiver element 114A, and a second screw implant 110B is shown with a receiver element 114B. An extension tube 210A is connected over implant 110A, and another extension tube 210B is connected over implant 110B. Implants 110A and 110B are implanted into adjacent vertebrae. A rod (not shown) will be inserted through implants 110A and 110B along a proposed path of trajectory T. In FIG. 10, receiver elements 114A and 114B are not aligned with trajectory T, and are not aligned with each other. This condition would prevent a rod from being inserted through implants 110A and 110B. To address this, an apparatus like apparatus 200 can be connected with implant 110A to rotate receiver element 114A in a clockwise direction A to steer its transverse passage 138A toward implant 110B. Apparatus 200 may also be connected with implant 110B to rotate receiver element 114B in a clockwise direction B to steer its transverse passage 138B toward implant 110A. Both receiver elements 114A and 114B can be steered toward one another and toward common trajectory T. FIG. 11 shows implants 110A, 110B and extension tubes 210A, 210B after the implants are steered toward one another in alignment with trajectory T. In this arrangement, transverse channels 138A, 238A, 138B, 238B are all aligned with trajectory T.

Where steering control member 250 is used, the steering control member may be attached to extension tube 210A and maneuvered to adjust the orientation and/or angular position of implant 110A. The steering control member 250 may then be disconnected from extension tube 210A, and connected to extension tube 210B, where it can be used to adjust the orientation and/or angular position of implant 110B.

The process of steering a receiver element can be carried out by applying one or more forces to steering control member 250. Forces may be applied to the main body 258, the handle 259 or both. Although handle 259 is shown in FIGS. 2 and 3 as a single knob configuration, handles may have a number of other configurations, including but not limited to L-shaped jug handles or finger loops. There may be a single handle, or multiple handles. On steering control member 250, for example, it will be understood that another handle identical to handle 259 may be placed on another side of the steering control member.

While preferred embodiments of the invention have been shown and described herein, it will be understood that such embodiments are provided by way of example only. Numerous variations, combinations, changes and substitutions will occur to those skilled in the art without departing from the scope of the invention.

For example, apparatus 200 was shown and described as an assembly of attachable components, including extension tube 210, steering control member 250, irrigation/suction trocar 300 and endoscope 400. Two or more of these components may be combined into a single integrated component of unitary construction, rather than an assembly of detachably coupled parts. The steering control member, for example, may have an elongated distal portion that functions as an extension tube that connects directly to the receiver element of the pedicle screw implant. This embodiment would eliminate the need for a separate extension tube. The endoscope and irrigation/suction device may then be inserted into the steering control member. Alternatively, the endoscope and irrigation/suction device may also be integrated with and built into the steering control member, forming a single standalone instrument that can be connected directly to a screw implant.

Another variation of apparatus 200 may include an extension tube that does not have slots or a transverse passage. In such a case, the receiver body is the only component with slots and a transverse passage. It may be desirable to have slots in the sidewall of the extension tube, as shown in the example in FIG. 6, because it provides a larger opening to introduce the rod to the receiver body. The slots in the extension tube also provide a larger opening through which the rod can be seen when an endoscope is used. Nevertheless, the extension tube or steering apparatus need not have sidewalls with slots that form transverse passages.

Accordingly, it is intended that the appended claims cover all such variations as fall within the scope of the invention.

What is claimed:

1. An apparatus for visualizing insertion of a fixation element into a screw implant, the apparatus comprising:
   an extension tube having a proximal end and a distal end opposite the proximal end, the proximal end of the extension tube having at least one slot defined therein and the distal end of the extension tube configured for coupling to a receiver element that has a transverse passage and is connected to a bone screw of the screw implant; and
   a steering control member comprising a proximal end, a distal end opposite the proximal end, a tubular extension extending from the proximal end of the steering control member to the distal end of the steering control member, and at least one elongated tab projecting along an outer surface of the tubular extension from a proximal end of the tubular extension toward a distal end of the tubular extension,
   wherein a distal end of the at least one elongated tab is positioned intermediate the proximal and distal ends of the tubular extension,
   wherein the at least one slot receives the at least one elongated tab therein and fixes the extension tube relative to the steering control member,
   wherein the tubular extension has a hollow interior, and
   wherein the tubular extension of the steering control member forms a plug, the plug having an outer diameter equal to or less than an inner diameter of the proximal end of the extension tube, wherein the plug is inserted into the proximal end of the extension tube in a snug fit.

2. The apparatus of claim 1, wherein the steering control member comprises a main body and a handle extending laterally from the main body, the main body forming a hollow interior that is in open communication with the hollow interior of the tubular extension.

3. The apparatus of claim 2, wherein the steering control member comprises a port in fluid communication with the hollow interior of the main body.

4. The apparatus of claim 1, wherein the at least one slot comprises a first slot and a second slot located opposite the first slot, and the at least one elongated tab comprises a first elongated tab and a second elongated tab located opposite the first elongated tab.

5. The apparatus of claim 1, wherein an outer diameter of the at least one elongated tab equals an outer diameter of the extension tube.

6. The apparatus of claim 1, further comprising a trocar having an elongated hollow shaft which extends through the steering control member and into the extension tube.

7. The apparatus of claim 6, further comprising an endoscope having an eyepiece and an elongated shaft, wherein the elongated shaft of the endoscope has an outer diameter that is less than an inner diameter of the elongated shaft of the trocar, and the elongated shaft of the endoscope extends through the elongated shaft of the trocar.

8. The apparatus of claim 7, wherein the elongated shaft of the trocar comprises a proximal end and a distal end opposite the proximal end, the distal end of the elongated shaft of the trocar being located intermediate the proximal and distal ends of the extension tube.

9. The apparatus of claim 8, wherein a distal end of the elongated shaft of the endoscope is located intermediate the distal end of the elongate shaft of the trocar and the proximal end of the extension tube.

10. The apparatus of claim 9, wherein the distal end of the elongated shaft of the trocar is located intermediate the distal end of the elongated shaft of the endoscope and the distal end of the extension tube.

11. The apparatus of claim 9, wherein the distal end of the elongated shaft of the endoscope comprises a lens.

12. The apparatus of claim 10, wherein the hollow interior of the extension tube defines a line of sight into the transverse passage of the receiver element.

13. The apparatus of claim 6, comprising an irrigation/suction device inserted through the steering control member and into the extension tube.

* * * * *